US006896897B2

(12) United States Patent
Farber

(10) Patent No.: US 6,896,897 B2
(45) Date of Patent: *May 24, 2005

(54) FLEXIBLE APPLICATOR FOR APPLYING OIL-IN-WATER EMULSION WITH IMPROVED STABILITY

(75) Inventor: Elliott Farber, North Mankato, MN (US)

(73) Assignee: Alwyn Company, Inc., Lake Crystal, MN (US)

( * ) Notice: Subject to any disclaimer, the term of this patent is extended or adjusted under 35 U.S.C. 154(b) by 150 days.

This patent is subject to a terminal disclaimer.

(21) Appl. No.: 09/939,816

(22) Filed: Aug. 27, 2001

(65) Prior Publication Data

US 2002/0102288 A1 Aug. 1, 2002

Related U.S. Application Data

(63) Continuation-in-part of application No. 09/360,095, filed on Jul. 23, 1999, now Pat. No. 6,281,236.

(51) Int. Cl.$^7$ .......................... A61K 9/107; A61K 7/00; A61K 9/113; A61K 31/4168

(52) U.S. Cl. ....................... 424/447; 424/443; 424/444; 424/445; 424/446; 424/401; 424/405; 424/70.22; 424/70.24; 424/70.31; 424/730; 424/70.23; 514/390; 514/939; 514/940; 514/941; 514/943

(58) Field of Search .................................. 424/447, 443, 424/444, 445, 446, 401, 405, 70.22, 70.24; 514/390, 937, 939, 940, 941, 943

(56) References Cited

U.S. PATENT DOCUMENTS

| | | |
|---|---|---|
| 3,830,824 A | 8/1974 | Margraf |
| 3,830,825 A | 8/1974 | Margraf |
| 3,830,908 A | 8/1974 | Klippel et al. |
| 3,856,805 A | 12/1974 | Margraf |
| 3,930,000 A | 12/1975 | Margraf |
| 3,932,627 A | 1/1976 | Margraf |
| 3,954,989 A | 5/1976 | Mecca |
| 4,170,229 A | 10/1979 | Olson |
| 4,278,664 A | 7/1981 | Van Cleave |
| 4,374,766 A | 2/1983 | Puchalski et al. |
| 4,478,853 A | 10/1984 | Chaussee |
| 4,507,279 A | 3/1985 | Okuyama et al. |
| 4,670,263 A | 6/1987 | Noorlander |
| 4,707,354 A | 11/1987 | Garlen et al. |
| 4,708,813 A | 11/1987 | Snyder |
| 4,806,262 A | 2/1989 | Snyder |
| 4,880,621 A | 11/1989 | Grollier et al. |
| 4,933,117 A * | 6/1990 | Grollier et al. ............... 424/74 |
| 4,981,845 A | 1/1991 | Pereira |
| 5,112,886 A | 5/1992 | Phalangas |
| 5,122,533 A | 6/1992 | Bar-On et al. |
| 5,176,916 A * | 1/1993 | Yamanaka et al. .......... 424/448 |
| 5,221,533 A | 6/1993 | Perlman |
| 5,455,033 A | 10/1995 | Silverman et al. |
| 5,476,664 A | 12/1995 | Robinson et al. |
| 5,512,200 A | 4/1996 | Garcia |
| 5,567,427 A | 10/1996 | Papadakis |
| 5,578,312 A | 11/1996 | Parrinello |
| 5,616,347 A | 4/1997 | Alliger et al. |
| 5,658,559 A | 8/1997 | Smith |
| 5,661,170 A | 8/1997 | Chodosh |
| 5,709,847 A | 1/1998 | Bissett et al. |
| 5,736,128 A | 4/1998 | Chaudhuri et al. |
| 5,824,666 A | 10/1998 | Deckner et al. |
| 5,827,870 A | 10/1998 | Chodosh |
| 5,830,483 A | 11/1998 | Seidel et al. |
| 5,849,310 A | 12/1998 | Trinh et al. |
| 5,863,548 A | 1/1999 | Elder |
| 5,871,754 A | 2/1999 | Briggs et al. |
| 5,871,762 A * | 2/1999 | Venkitaraman et al. ..... 424/402 |
| 5,876,736 A | 3/1999 | Cohen et al. |
| 5,885,581 A | 3/1999 | Massand |
| 5,914,116 A | 6/1999 | Suares et al. |
| 5,932,228 A | 8/1999 | Hall et al. |
| 5,952,373 A | 9/1999 | Lanzendörfer et al. |
| 5,958,436 A | 9/1999 | Hahn et al. |
| 5,968,528 A | 10/1999 | Deckner et al. |
| 6,001,377 A | 12/1999 | SaNogueira, Jr. et al. |
| 6,060,061 A | 5/2000 | Breton et al. |

(Continued)

FOREIGN PATENT DOCUMENTS

| | | |
|---|---|---|
| EP | 0242553 | 10/1987 |
| EP | 0380157 | 8/1990 |
| GB | 1346544 | 2/1974 |
| JP | 358140013 A | 8/1983 |
| JP | 404208219 | 7/1992 |
| WO | WO 90/09779 | 9/1990 |

OTHER PUBLICATIONS

Registry Copyright 2002 ACS, RN 99–76–3 and RN 94–13–3.*

(Continued)

*Primary Examiner*—Russell Travers
*Assistant Examiner*—Shahnam Sharareh
(74) *Attorney, Agent, or Firm*—Hogan & Hartson LLP

(57) ABSTRACT

A flexible applicator for applying an oil-in-water emulsion comprises: (1) an allantoin-containing oil-in-water emulsion; and (2) a flexible element that adsorbs or absorbs the emulsion such that the emulsion is applied to the skin of a patient on whom the flexible applicator is placed. The allantoin-containing emulsion, containing allantoin and an emulsifier, has improved stability coming from the adjustment of the pH to a range of 3.0 to 6.0; preferably, the pH is in the range of 4.5 to about 5.8. The lower pH preserves the stability of the allantoin and the functionality of the emulsifier system is maintained. The emulsifier system can be a nonionic emulsifier or an anionic emulsifier plus beeswax. The acid used to adjust the pH can be an organic acid or an inorganic acid. The emulsion can further comprise other ingredients such as herbal extracts, chelating agents, preservatives, emollients, solvents, and fragrance. The flexible element can be in the form of a bandage or wipe, and can be formed of a material such as cotton, cellulose, nylon, rayon, a non-woven fabric, or a plastic polymer.

19 Claims, No Drawings

U.S. PATENT DOCUMENTS

| | | | |
|---|---|---|---|
| 6,080,393 | A | 6/2000 | Liu et al. |
| 6,086,903 | A | 7/2000 | Trinh et al. |
| 6,120,782 | A | 9/2000 | Mansouri |
| 6,174,533 | B1 | 1/2001 | SaNogueira, Jr. et al. |
| 6,281,236 | B1 * | 8/2001 | Farber .................. 514/390 |
| 6,306,915 | B1 | 10/2001 | Murata |
| 6,337,065 | B1 | 1/2002 | Jacobson et al. |

OTHER PUBLICATIONS

Product information insert for Alphosyl Cream and Alphosyl Lotion, G.D. Searle (South Africa), Apr. 24, 1975.
Product information insert for Clearsil Mediated Facial Cleanser, Procter & Gamble (South Afrida), Jan. 31, 199.
Product information insert for Arola Rosebaum Ointment, Supramed Limited, Jan. 12, 1986.
Abstract of a publication, M. Cajkovac et al., "Influence of Emulsoid Vehicle on the Release and Activity of Allantoin," *Pharmacie* 47 :39–43 (1992) (abstract only).
Abstract of a publication, M. Maragakis et al., "Possibilities of Scar Treatment After Thoracic Surgery," *Drugs Under Exp. & Clin. Res.* 21:199–206 (1995) (abstract only).
Product information insert for Alphosyl, undated.
Abstract of a publication, G. Stinco et al., "Seborrheic Dermatitis Treated with Furalglucitole Cream," *Dermatol. Clin.* 18:78–81 (1998) (abstract only).
Abstract of a publication, G.H. Willital & H. Heine, "Efficiency of Contractubex® Gel in the Treatment of Fresh Scars After Thoracic Surgery in Children and Adolescents," *Int. J. Clin Pharmacol. Res.* 14:193–202 (1994) (abstract only).
H.W. Margraf & T.H. Covey, Jr., "A Trial of Silver–Zinc–Allantoinate in the Treatment of Leg Ulcers," *Arch. Surg.* 12:699–704 (1977).
Remington: The Science and Practice of Pharmacy (19$^{th}$ Ed. 1995, Mack Publishing Co., Easton, Pennsylvania), pp. 639–640, 1380.
D. Hoffmann, "The Complete Illustrated Herbal," (Barnes and Noble, 1996), pp. 63, 104.
F.R. Greenbaum, "The Story of Allantoin," *Am. J. Pharm.* 112:205–216 (1940).
M.A. Lesser, "Allantoin," *Drug Cosmet. Ind.* 42:451–456, 469 (1938).
I.I. Lubowe & S.B. Mecca, "Allantoin and Aluminum Derivatives in Dermatological Applications,g" *Drug Cosmet. Ind.* 84:36, 37, 117 (1959).
S.B. Mecca, "Allantoin anda the Newer Aluminum Allantoinates," *Proc. Scient. Sect. Toilet Goods Assoc.* No. 31: 1–6 (1959).
S.B. Mecca, "The Function and Applicability of the Allantoins," *Proc. Scient. Sect. Toilet Goods Assoc.* No. 39: 7–15 (1963).

P. LeVan, "The Use of Silicones in Dermatology," *Calif. Med.* 81:210–213 (1954).

R. Cahen & A. Pessonnier, "Etude Pharmacologique de L'Allantoïnatede Dihydroxyaluminium et de L'Allantoïnate de Chlorhydroxyaluminium. 1.—Toxicité," *Ann. Pharm. Franc.* 20: 623–636 (1962) (in French), discloses the physical and chemical properties and the toxicity of dihydroxyaluminum allantoinate and chlorhydroxyaluminum allantoinate. The compounds were observed to have no toxicity.

R. Cahen & J.–F. Clement, "Etude Pharmacologique de L'Allantoïnate de Dihydroxyaluminium et de L'Allantoïnat de Chlorhydroxyaluminium. II.—Etude de l'Activité Gastrique," *Ann. Pharm. Franc.* 20: 693–703 (1962) (in French), discloses the activity of dihydroxyaluminum allantoinate and chlorhydroxyaluminum allantoinate on gastri activity. The compounds were found to have acid–neutralizing and buffering activity and to diminish gastric acidity.

R. Cahen & A. Pessonnier, "Etude Pharmacologique de L'Allanoïnate de Dihydroxyaluminium et de L'Allantoïnate de Chlorhydroxyaluminium. III—Effet Anti–ulcéreux," *Ann. Pharm. Franc.* 20: 704–713 (1962) (in French), discloses the anti–ulcer activity of the compounds dihydroxyaluminum allantoinate and chlorhydroxyaluminum allantoinate. The compounds were found to have anti–ulcer activity in rats and guinea pigs comparable to compounds such as aluminum hydrate and bismuch subnitrate.

R. Cahen & A. Pessonnier, "Etude Pharmacologique de L'Allantoïnate de Dihydroxyaluminum et de L'Allatoïnate de Chlorhydroxyaluminium. IV.—Effet sur l'Ulcère Médicamenteux Expérimental," *Ann. Pharm. Franc.* 21: 215–222 (1963) (in French), discloses the effect of the compounds dihydroxyaluminum allantoinate and chlorhydroxyaluminum allantoinate on ulcers produced in the rat by administration of phenylbutazone or reserpine. The compounds were found to have activity against such ulcers.

C. Debray et al., "Etude de Dèrivés Allantoïniques de l'Aluminium dans la Thérapeutique des Affections Gastro–duodénales," *Presse Méd.* 70: 2643–2644 (1962) (in French) discloses the activity of the compounds dihydroxyaluminum allantoinate and chlorhydroxyaluminum allantoinate administered in a complex with a polymer of polyoxyethylene and polyoxypropanediol, methylhomatropine bromide, and calcium carbonate on gastrointestina conditions. The complex was said to be effective against duodenal ulcer and effective in protecting the gastric mucosa.

* cited by examiner

FLEXIBLE APPLICATOR FOR APPLYING OIL-IN-WATER EMULSION WITH IMPROVED STABILITY

CROSS-REFERENCES

This application is a continuation-in-part of application Ser. No. 09/360,095, by Elliott Farber, entitled "Oil-in-Water Emulsion with Improved Stability," filed Jul. 23, 1999, now U.S. Pat. No. 6,281,236 hereby incorporated in its entirety by this reference.

BACKGROUND OF THE INVENTION

1. Field of the Invention

This invention is directed to flexible applicators for applying an oil-in-water emulsion in which allantoin has improved stability, particularly for cosmetic and over-the-counter drug applications.

2. General Background and State of the Art

Allantoin is a commonly used ingredient in cosmetic applications, particularly for skin creams, where it exerts a skin protective function. Many such cosmetic compositions are prepared as emulsions, particularly oil-in-water emulsions. One emulsifier system used with such compositions is a combination of sodium lauryl sulfate and beeswax. Although solutions of sodium lauryl sulfate are alkaline with an approximate pH of 9.5, the simultaneous use of beeswax with its organic acids produces a complex and neutralized system with a pH of about 6.8 to about 7.5. However, in such a system with a pH range of 6.8 to 7.5, allantoin degrades significantly with time in an accelerated stability test at 40° C. Because cosmetics are typically stored by users at room temperature, and room temperatures can fluctuate with climatic conditions, such a degree of instability is undesirable. Therefore, there is a need for an oil-in-water emulsified composition containing allantoin that uses the sodium lauryl sulfate-beeswax emulsion system in which the stability of allantoin is increased.

Moreover, there is a need for efficient and readily accepted applicators for such emulsions. The direct manual application of such emulsions to the skin of a patient can be messy and inefficient, and even health care professionals may be reluctant to perform such application to the skin of a patient who has open sores and is suffering from a blood-borne communicable disease such as AIDS or hepatitis C, to name only two of a number of such conditions. Accordingly, there is a particular need for an applicator that can apply such emulsions reliably and reproducibly to the skin of a patient. There is a further need for an applicator that can retain the emulsion on the skin of a patient for the desired time period.

INVENTION SUMMARY

A flexible applicator for applying an oil-in-water emulsion that meet these needs comprises:

(1) an allantoin-containing oil-in-water emulsion as described below; and (2) a flexible element that adsorbs or absorbs the emulsion such that the emulsion is applied to the skin of a patient on whom the flexible applicator is placed.

The allantoin-containing emulsion uses an emulsification system in which the pH is adjusted to from about 3.0 to about 6.0 with the use of a small amount of acid. Preferably, the pH is adjusted to a range of from about 4.5 to about 5.8. The allantoin is stable in the emulsion for at least 90 days at 40° C.

The emulsification system can include beeswax and an anionic emulsifier that is substantially hydrophilic and is soluble in water. Alternatively, the emulsification system can include a nonionic emulsifier that is an ethoxylated ether or an ethoxylated ester whose carbon chain length ranges from 8 to 22 carbon atoms.

One embodiment of an emulsion useful in a flexible applicator according to the present invention comprises:

(1) allantoin; and (2) an emulsifier system including beeswax and an anionic emulsifier that is substantially hydrophilic and is soluble in water; and (3) an acid to adjust the pH of the emulsion to a value from about 3.0 to about 6.0. Preferably, the pH of the emulsion is from about 4.5 to about 5.8.

The emulsifier can be selected from the group consisting of ammonium lauryl sulfate, sodium lauryl sulfate, sodium laureth sulfate, sodium oleyl succinate, ammonium lauryl sulfosuccinate, sodium dodecylbenzenesulfonate, ammonium laureth sulfate, and sodium lauryl sarcosinate. In one preferred embodiment, the emulsifier is sodium lauryl sulfate.

The emulsion can comprise at least one organic acid of from 2 to 22 carbon atoms. The organic acid can be citric acid, ascorbic acid, glycolic acid, lactic acid, benzoic acid, or salicylic acid. Alternatively, the emulsion can comprise at least one inorganic acid selected from the group consisting of hydrochloric acid, sulfuric acid, and phosphoric acid. The emulsion can comprise both organic and inorganic acids.

Another embodiment of an emulsion useful in a flexible applicator according to the present invention comprises:

(1) allantoin;

(2) an emollient component comprising:
  (a) lanolin oil;
  (b) cetyl alcohol;
  (c) stearyl alcohol;
  (d) cod liver oil;
  (e) butylated hydroxytoluene;

(3) an emulsifier system comprising at least one nonionic emulsifier that is an ethoxylated ether or an ethoxylated ester whose carbon chain length ranges from 8 to 22 carbon atoms; and (4) at least one acid selected from the group consisting of:
  (a) an organic acid of from 2 to 22 carbon atoms; and
  (b) an inorganic acid selected from the group consisting of hydrochloric acid, sulfuric acid, and phosphoric acid to adjust the pH to from about 3.0 to about 6.0. Preferably, the pH of the emulsion is from about 4.5 to about 5.8.

Yet another embodiment of an emulsion useful in a flexible applicator according to the present invention comprises:

(1) allantoin; and (2) an emulsifier system including at least one nonionic emulsifier that is an ethoxylated ether or an ethoxylated ester whose carbon chain length ranges from 8 to 22 carbon atoms; and (3) an acid to adjust the pH of the emulsion to a value from about 3.0 to about 6.0. Preferably, the pH of the emulsion is from about 4.5 to about 5.8.

The emulsion can further include a number of ingredients. These ingredients can include the following:

(1) an emollient component that is one or more of lanolin oil, cetyl alcohol, stearyl alcohol, cod liver oil, and butylated hydroxytoluene;

(2) herbal extracts, including one or more of St. John's wort extract, witch hazel extract, chamomile extract, and arnica extract;

(3) a preservative component that is one or more of methylparaben and propylparaben; and (4) a solvent component that is one or more of propylene glycol, glycerol, or butylene glycol, and is preferably propylene glycol.

One preferred emulsion useful in a flexible applicator according to the present invention comprises:

(1) water;
(2) sodium lauryl sulfate;
(3) propylene glycol;
(4) tetrasodium EDTA;
(5) citric acid;
(6) lanolin oil;
(7) cetyl alcohol;
(8) stearyl alcohol;
(9) beeswax;
(10) cod liver oil;
(11) butylated hydroxytoluene;
(12) St. John's wort extract;
(13) witch hazel extract;
(14) chamomile extract;
(15) arnica extract;
(16) methylparaben;
(17) propylparaben;
(18) allantoin; and
(19) fragrance;

where the pH of the emulsion is from about 3.0 to about 6.0. Preferably, the pH of the emulsion is from about 4.5 to about 5.8.

A more preferred emulsion useful in a flexible applicator according to the present invention comprises:

(1) from about 50% to about 90% of water;
(2) from about 0.5% to about 2.5% of 30% sodium lauryl sulfate;
(3) from about 2.0% to about 9.0% of propylene glycol;
(4) from about 0.05% to about 0.50% of tetrasodium EDTA;
(5) from about 0.05% to about 0.5% of citric acid;
(6) from about 5% to about 15% of lanolin oil;
(7) from about 3% to about 10% of cetyl alcohol;
(8) from about 1% to about 5% of stearyl alcohol;
(9) from about 0.5% to about 2.5% of beeswax;
(10) from about 1.0% to about 7.0% of cod liver oil;
(11) from about 0.1% to about 1.0% of butylated hydroxytoluene;
(12) from about 0.05% to about 0.50% of St. John's wort extract;
(13) from about 0.05% to about 0.50% of witch hazel extract;
(14) from about 0.05% to about 0.5% of chamomile extract,
(15) from about 0.05% to about 0.5% of arnica extract;
(16) from about 0.1% to about 0.5% of methylparaben;
(17) from about 0.1% to about 0.5% of propylparaben;
(18) from about 0.50% to about 2% of allantoin; and
(19) from about 0.05% to about 0.50% of fragrance;

the pH of the emulsion being from about 3.0 to about 6.0. Preferably, the pH of the emulsion is from about 4.5 to about 5.8.

A still more preferred emulsion useful in a flexible applicator according to the present invention comprises:

(1) from about 55% to about 75% of water;
(2) from about 1.0% to about 2.5% of 30% sodium lauryl sulfate;
(3) from about 3.0% to about 6.0% of propylene glycol;
(4) from about 0.1% to about 0.3% of tetrasodium EDTA;
(5) from about 0.08% to about 0.35% of citric acid;
(6) from about 8.0% to about 12.0% of lanolin oil;
(7) from about 3.5% to about 7.5% of cetyl alcohol;
(8) from about 1.0% to about 3.0% of stearyl alcohol;
(9) from about 1.0% to about 2.5% of beeswax;
(10) from about 1.0% to about 4.0% of cod liver oil;
(11) from about 0.2% to about 0.8% of butylated hydroxytoluene;
(12) from about 0.05% to about 0.15% of St. John's wort extract;
(13) from about 0.05% to about 0.15 % of witch hazel extract;
(14) from about 0.05% to about 0.15% of chamomile extract;
(15) from about 0.05% to about 0.15% of arnica extract;
(16) from about 0.15% to about 0.40% of methylparaben;
(17) from about 0.10% to about 0.30% of propylparaben;
(18) from about 0.50% to about 2.0% of allantoin; and
(19) from about 0.1% to about 0.3% of fragrance;

the emulsion having a pH of from about 3.0 to about 6.0. Preferably, the pH of the emulsion is from about 4.5 to about 5.8.

A still more preferred emulsion useful in a flexible applicator according to the present invention comprises:

(1) about 68.68% of water;
(2) about 1.9% of 30% sodium lauryl sulfate;
(3) about 5.3% of propylene glycol;
(4) about 0.15% of tetrasodium EDTA;
(5) about 0.12% of citric acid;
(6) about 10.6% of lanolin oil;
(7) about 4.2% of cetyl alcohol;
(8) about 2.0% of stearyl alcohol;
(9) about 1.90% of beeswax;
(10) about 2.0% of cod liver oil;
(11) about 0.5% of butylated hydroxytoluene;
(12) about 0.1% of St. John's wort extract;
(13) about 0.1% of witch hazel extract;
(14) about 0.1% of chamomile extract;
(15) about 0.1% of arnica extract;
(16) about 0.3% of methylparaben;
(17) about 0.25% of propylparaben;
(18) about 1.50% of allantoin; and
(19) about 0.20% of fragrance;

the emulsion having a pH of from about 3.0 to about 6.0. Preferably, the pH of the emulsion is from about 4.5 to about 5.8.

The flexible element of the flexible applicator can be in the form of a bandage or a wipe.

The flexible element of the flexible applicator can be formed of a material selected from the group consisting of cotton, cellulose, nylon, rayon, a non-woven fabric, and a plastic polymer.

DETAILED DESCRIPTION OF THE PREFERRED EMBODIMENTS

A flexible applicator for applying an oil-in-water emulsion comprises:

(1) an allantoin-containing oil-in-water emulsion as described below; and (2) a flexible element that adsorbs or absorbs the emulsion such that the emulsion is applied to the skin of a patient on whom the flexible applicator is placed.

The allantoin-containing oil-in-water emulsion, which is described in further detail below, has improved stability properties such that the allantoin is stable in the emulsion for at least 90 days at 40° C.

The allantoin-containing emulsion uses an emulsification system including either: (1) beeswax and an anionic emulsifier that is substantially hydrophilic or (2) a nonionic emulsifier that is an ethoxylated ether or an ethoxylated ester whose carbon chain length ranges from 8 to 22 carbon atoms, in which the pH is adjusted to from about 3.0 to about 6.0 with the use of a small amount of acid. Preferably, the pH is adjusted to from about 4.5 to about 5.8. As shown below in Example 4, the stability of allantoin at 40° C. is greatly improved while simultaneously maintaining the functionality of the emulsion system. This result is unexpected because acid can hydrolyze emulsifiers such as sodium lauryl sulfate.

Therefore, the emulsion employed in the flexible applicator of the present invention is an oil-in-water emulsion that includes allantoin and an emulsifier system that includes either: (1) beeswax and an anionic emulsifier system or (2) a nonionic emulsifier system.

If the emulsifier system is a nonionic emulsifier system, the emulsifier typically comprises ethoxylated ethers or ethoxylated esters whose carbon chain lengths range from 8 to 22 carbon atoms.

If the emulsifier system includes anionic emulsifiers, the anionic emulsifiers are substantially hydrophilic and are soluble in water. The anionic emulsifier is typically one of ammonium lauryl sulfate, sodium laureth sulfate, sodium oleyl succinate, ammonium lauryl sulfosuccinate, sodium dodecylbenzenesulfonate, ammonium laureth, sodium N-lauryl sarcosinate, or sodium lauryl sulfate. A particularly preferred anionic emulsifier is sodium lauryl sulfate.

The emulsion further includes an acid to reduce the pH to a pH in a range from about 3.0 to about 6.0; preferably, the pH is in a range from about 4.5 to about 5.8. The acid can be an organic acid, an inorganic acid, or a mixture of both.

Preferred organic acids include organic acids whose carbon chain length ranges from 2 to 22 carbon atoms and can be monocarboxylic, dicarboxylic, or tricarboxylic acids. The acids can be aliphatic or aromatic. Particularly preferred organic acids include citric acid, ascorbic acid, glycolic acid, lactic acid, benzoic acid, and salicylic acid. A most particularly preferred organic acid is citric acid.

Typically, the inorganic acid is a strong acid. It can be a monoprotic, diprotic, or triprotic acid. Particularly preferred inorganic acids include hydrochloric acid, sulfuric acid, and phosphoric acid.

One particular example of the emulsion is:

(1) allantoin; and (2) an emulsifier system including beeswax and an anionic emulsifier that is substantially hydrophilic and is soluble in water; and (3) an acid to adjust the pH of the emulsion to a value from about 3.0 to about 6.0.

Another particular example of the emulsion is:

(1) allantoin;

(2) an emollient component comprising:
   (A) lanolin oil;
   (B) cetyl alcohol;
   (C) stearyl alcohol;
   (D) cod liver oil;
   (E) butylated hydroxytoluene;

(3) an emulsifier system comprising at least one nonionic emulsifier that is an ethoxylated ether or an ethoxylated ester whose carbon chain length ranges from 8 to 22 carbon atoms; and (4) at least one acid selected from the group consisting of:
   (A) an organic acid of from 2 to 22 carbon atoms; and
   (B) an inorganic acid selected from the group consisting of hydrochloric acid, sulfuric acid, and phosphoric acid to adjust the pH to from about 3.0 to about 6.0.

Yet another particular example of the emulsion is:

(1) allantoin; and (2i) an emulsifier system including at least one nonionic emulsifier that is an ethoxylated ether or an ethoxylated ester whose carbon chain length ranges from 8 to 22 carbon atoms; and (3) an acid to adjust the pH of the emulsion to a value from about 3.0 to about 6.0.

Other examples of emulsions can be used.

The emulsion can further include other ingredients. For example, the emulsion can include an emollient component for smoothness. The emollient component can include at least one of lanolin oil, cetyl alcohol, stearyl alcohol, cod liver oil, and butylated hydroxytoluene. Preferably, the emollient component comprises all of lanolin oil, cetyl alcohol, stearyl alcohol, cod liver oil, and butylated hydroxytoluene.

The emulsion can further include a solvent component. Typically, the solvent component is one or more of propylene glycol, glycerin, or butylene glycol. Preferably, the solvent component is propylene glycol.

The emulsion can further include a chelating agent to bind metal ions that might accelerate degradation of the emulsion. A particularly preferred chelating agent is EDTA. The EDTA can be added in various acid or salt forms depending on the pH of the composition, such as EDTA itself, disodium EDTA, or tetrasodium EDTA.

The emulsion can further include herbal extracts. The herbal extracts can include one or more of St. John's wort extract, witch hazel extract, chamomile extract, and arnica extract. Preferably, the emulsion includes all of St. John's wort extract, witch hazel extract, chamomile extract, and arnica extract.

The emulsion can further include a preservative such as methylparaben, ethylparaben, propylparaben, butylparaben, or phenoxyethanol. Preferably, the emulsion comprises methylparaben and propylparaben as preservatives.

The emulsion can further include fragrance. The use of fragrance is well known in the cosmetic art and in the art of over-the-counter drug formulation, and many suitable fragrances are known in the art. The stability and function of the emulsion is not altered by the presence or absence of fragrance.

The emulsion can further include other components, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

The following discussion describes ranges, preferred concentrations, and optimum concentrations for preferred emulsions according to the present invention. All percentages recited herein are weight percent unless otherwise specified.

Water can comprise from about 50% to about 90% of the emulsion. Preferably, water comprises from about 55% to about 75% of the emulsion. An optimum concentration of water is about 68.68%.

Sodium lauryl sulfate, as a 30% solution, can comprise from about 0.5% to about 2.5% of the emulsion. Preferably, sodium lauryl sulfate comprises from about 1.0% to about 2.5% of the emulsion. An optimum concentration of sodium lauryl sulfate in the emulsion is about 1.9%.

Propylene glycol can comprise from about 2.0% to about 9.0% of the emulsion. Preferably, propylene glycol comprises from about 3.0% to about 6.0% of the emulsion. An optimum concentration of propylene glycol is about 5.3% of the emulsion.

Tetrasodium EDTA can comprise from about 0.05% to about 0.50% of the emulsion. Preferably, tetrasodium EDTA comprises from about 0.10% to about 0.30% of the emulsion. An optimum concentration of tetrasodium EDTA is 0.15% of the emulsion.

Citric acid can comprise from about 0.05% to about 0.50% of the emulsion. A preferred concentration of citric acid is from about 0.08% to about 0.35% of the emulsion. An optimum concentration of citric acid is about 0.12%.

Lanolin oil can comprise from about 5.0% to about 15.0% of the emulsion. Preferably, lanolin oil comprises from about 8.0% to about 12.0% of the emulsion. An optimum concentration of lanolin oil is about 10.60% of the emulsion.

Cetyl alcohol can comprise from about 3.0% to about 10.0% of the emulsion. A preferred concentration of cetyl alcohol is from about 3.5% to about 7.5% of the emulsion. An optimum concentration of cetyl alcohol is about 4.2% of the emulsion.

Stearyl alcohol can comprise from about 1.0% to about 5.0% of the emulsion. A preferred concentration of stearyl alcohol is from about 1.0% to about 3.0% of the emulsion. An optimum concentration of stearyl alcohol is about 2.0% of the emulsion.

Beeswax can comprise from about 0.5% of the emulsion to about 2.5% of the emulsion. A preferred concentration of beeswax is about 1.0% to about 2.5% of the emulsion. An optimum concentration of beeswax is about 1.9% of the emulsion.

Cod liver oil can comprise from about 1.0% to about 7.0% of the emulsion. Preferably, cod liver oil comprises from about 1.0% to about 4.0% of the emulsion. An optimum concentration of cod liver oil is about 2.0% of the emulsion.

Butylated hydroxytoluene can comprise from about 0.1% to about 1.0% of the emulsion. Preferably, butylated hydroxytoluene comprises from about 0.2% to about 0.8% of the emulsion. An optimum concentration of butylated hydroxytoluene is about 0.50% of the emulsion.

St. John's wort extract can comprise from about 0.05% to about 0.5% of the emulsion. Preferably, St. John's wort extract comprises from about 0.05% to about 0.15% of the emulsion. An optimum concentration of St. John's wort extract is about 0.10% of the emulsion.

Witch hazel extract can comprise from about 0.05% to about 0.5% of the emulsion. Preferably, witch hazel extract comprises from about 0.05% to about 0.15% of the emulsion. An optimum concentration of witch hazel extract is about 0.10% of the emulsion.

Chamomile extract can comprise from about 0.05% to about 0.50% of the emulsion. A preferred concentration of chamomile extract is from 0.05% to about 0.15% of the emulsion. An optimum concentration of chamomile extract is about 0.10% of the emulsion.

Arnica extract can comprise from about 0.5% to about 0.50% of the emulsion. Preferably, arnica extract comprises from about 0.05% to about 0.15% of the emulsion. An optimum concentration of arnica extract is about 0.10% of the emulsion.

Methylparaben can comprise from about 0.10% to about 0.50% of the emulsion. A preferred concentration of methylparaben is from 0.15% to about 0.40% of the emulsion. An optimum concentration of methylparaben is about 0.30% of the emulsion.

Propylparaben can comprise from about 0.10% to about 0.50% of the emulsion. Preferably, propylparaben comprises from about 0.10% to about 0.30% of the emulsion. An optimum concentration of propylparaben is about 0.25% of the emulsion.

Allantoin can comprise from about 0.50% to about 2.0% of the emulsion. A preferred concentration of allantoin is from about 0.50% to about 2.0% of the emulsion. An optimum concentration of allantoin is about 1.50% of the emulsion.

Fragrance can comprise from about 0.05% of the emulsion to about 0.50% of the emulsion. Preferably, fragrance comprises from about 0.10% of the emulsion to about 0.30% of the emulsion. An optimum concentration of fragrance is about 0.20% of the emulsion.

The emulsion is prepared by standard mixing techniques, such as are conventional in the cosmetic art for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components. Further details of preparation of the emulsion are described in Example 2.

The flexible element of the present invention is typically in the form of a bandage or of a wipe. Alternative physical forms of the flexible element can be used. The shape and size of the bandage or wipe can be chosen to suit particular needs or for application to specific anatomical locations. The bandage can be in the form of a narrow strip or a square or rectangular patch.

The flexible element of the present invention can be formed of cotton, gauze, cellulose, nylon, rayon, a nonwoven fabric, or a plastic polymer that absorbs or adsorbs the emulsion for application. Suitable materials are generally known in the art and are commonly used for bandages, dressings, and wipes.

The flexible element of the present invention can further include a backing that is typically prepared from a plastic polymer for ease of application. Such backings are generally known in the art. Such backings can include an adhesive for adhering the flexible applicator to the skin of a patient to retain the emulsion on the skin. The backing can be porous to enable the flexible element to "breathe" and not allow moisture to build up between the skin and the flexible element so that the flexible element is retained on the skin for such time as it is needed. Such construction is well known and is generally used in the art.

The flexible element of the present invention can be packaged in a sealed envelope or container for storage and use as needed.

In the manufacture of a flexible applicator according to the present invention, when manufacture of the emulsion is completed, the emulsion is typically at a temperature of about 120° F. and is still fluid. The emulsion can be applied at that temperature to a gauze or other suitable flexible element, using a knife edge or other application tool. As the gauze or other suitable flexible element travels down a production line, it cools and the emulsion solidifies. The flexible applicator can then be encased in a protective film and wound up. It can then be unwound for use.

The invention is illustrated by the following Examples. These examples are for illustrative purposes only and are not intended to limit the invention.

EXAMPLES

Example 1

Preparation of Skin Protectant Over-the-Counter Emulsion with pH of 7.4 (Prior Art Example)

A skin protectant over-the-counter (OTC) cream was prepared as an emulsion in accordance with the formulation of Table 1.

TABLE 1

COMPOSITION OF ALLANTOIN-CONTAINING EMULSION WITH pH OF 7.4

| INGREDIENT | RANGE | PREFERRED | OPTIMUM |
|---|---|---|---|
| Part A | | | |
| Water | 50.0–90.0 | 55.0–75.0 | 66.20 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Part B | | | |
| Lanolin Oil | 5.0–15.0 | 8.0–12.0 | 10.60 |
| Cetyl Alcohol | 3.0–10.0 | 3.5–7.5 | 6.80 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was then added to the Part A mixture with mixing. The resulting mixture was then cooled to 120° F. with continued mixing. The Part C ingredients were then added with mixing. The final emulsion was allowed to cool with continued mixing. The resulting cream had a pH of 7.4. Samples of the cream prepared from Example 1 were used for accelerated aging stability studies and analyzed for their allantoin concentration after a period of time at 40° C. The results are shown in Table 2.

As can be seen from Table 2, the allantoin in the cream from Example 1 undergoes degradation and would not meet the specifications required for an OTC drug.

TABLE 2

STABILITY OF ALLANTOIN IN SKIN CREAM COMPOSITION OF EXAMPLE 1 WITH STORAGE AT 40° C.

| Days at 40° C. | Weight % Allantoin |
|---|---|
| 0 | 1.5 |
| 30 | 1.4 |
| 60 | 1.3 |
| 90 | 1.2 |

Example 2

Preparation of an Emulsion Containing Allantoin with Lower pH

An OTC skin cream containing allantoin was prepared as an emulsion using the ingredients in Table 3 to provide a cream with a lower pH.

TABLE 3

COMPOSITION OF ALLANTOIN-CONTAINING EMULSION WITH pH OF 5.3

| INGREDIENT | RANGE | PREFERRED | OPTIMUM |
|---|---|---|---|
| Part A | | | |
| Water | 50.0–90.0 | 55.0–75.0 | 68.68 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Citric Acid | 0.05–0.50 | 0.08–0.35 | 0.12 |
| Part B | | | |
| Lanolin Oil | 5.0–15.0 | 8.0–12.0 | 10.60 |
| Cetyl Alcohol | 3.0–10.0 | 3.5–7.5 | 4.20 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was added to the Part A mixture with mixing. The resulting mixture was then cooled to 120° F. with mixing at which time the Part C ingredients were added with mixing. The final emulsion was allowed to cool with continue mixing. The resulting cream had a pH of 5.3.

It was found that a similar cream was produced if Part B was added to Part A or Part A was added to Part B. However, the cream has a better appearance if the oil phase and water phase are homogenized under high shear after the two phases are added to one another.

Samples of the cream of this example were used for accelerated aging stability studies and analyzed for their allantoin concentration. The results are shown in Table 4. As can be seen from Table 4, the allantoin is stable over time in a cream with a pH of 5.3.

TABLE 4

STABILITY OF ALLANTOIN IN EMULSION OF EXAMPLE 2 WITH STORAGE AT 40° C.

| Days at 40° C. | Weight % Allantoin |
|---|---|
| 0 | 1.4 |
| 30 | 1.4 |
| 60 | 1.4 |
| 90 | 1.4 |

Advantages of the Present Invention

The present invention provides a flexible applicator for applying an allantoin-containing emulsion that is an oil-in-water emulsion using either beeswax and an anionic emulsifier or a nonionic emulsifier to the skin of a patient. The emulsion has improved thermal stability. The emulsion shows no degradation of allantoin after three months of storage at 40° C. The emulsion also preserves the desirable properties of the beeswax and emulsifier systems without causing degradation of the allantoin. The emulsion applied by the flexible applicator is suitable for cosmetic and over-the-counter drug uses.

The flexible applicator provides an efficient means for applying the emulsion to the skin of a patient. It can be used either by the patient himself, or by a health professional, and is neater and more efficient than direct manual application of the emulsion. Furthermore, use of the flexible applicator reduces the risk of possible transmission of a blood-borne infection or disease when the applicator is used to apply the emulsion to a patient with open sores.

Although the present invention has been described in considerable detail, with reference to certain preferred versions thereof, other versions and embodiments are possible. Therefore, the scope of the invention is determined by the following claims.

While the specification describes particular embodiments of the present invention, those of ordinary skill can devise variations of the present invention without departing from the inventive concept.

I claim:

1. A flexible applicator system for applying an oil-in-water emulsion comprising:
    (a) an oil-in-water emulsion comprising:
        (i) water;
        (ii) sodium lauryl sulfate;
        (iii) propylene glycol;
        (iv) tetrasodium EDTA;
        (v) citric acid;
        (vi) lanolin oil;
        (vii) cetyl alcohol;
        (viii) stearyl alcohol;
        (ix) beeswax,
        (x) cod liver oil;
        (xi) butylated hydroxytoluene;
        (xii) St. John's wort extract;
        (xiii) witch hazel extract;
        (xiv) chamomile extract;
        (xv) arnica extract;
        (xvi) methylparaben;
        (xvii) propylparaben
        (xviii) over 0.40% of allantoin; and
        (xix) fragrance;
    wherein the pH of the emulsion is from about 4.5 to about 5.8, the allantoin being stable in the emulsion for at least 90 days at 40° C.; and
    (b) a flexible element that adsorbs or absorbs the emulsion such that the emulsion is applied to the skin of a patient on whom the flexible applicator is placed.

2. A flexible applicator system for applying an oil-in-water emulsion comprising:
    (a) an oil-in-water emulsion comprising:
        (i) from about 50% to about 90% water;
        (ii) from about 0.5% to about 2.5% of 30% sodium lauryl sulfate;
        (iii) from about 2.0% to about 9.0% of propylene glycol;
        (iv) from about 0.05% to about 0.50% of tetrasodium EDTA;
        (v) from about 0.05% to about 0.5% citric acid;
        (vi) from about 5% to about 15% lanolin oil;
        (vii) from about 3% to about 10% of cetyl alcohol;
        (viii) from about 1% to about 5% of stearyl alcohol;
        (ix) from about 0.5% to about 2.5% of beeswax,
        (x) from about 1.0% to about 7.0% of cod liver oil;
        (xi) from about 0.1% to about 1.0% of butylated hydroxytoluene;
        (xii) from about 0.05% to about 0.50% of St. John's wort extract;
        (xiii) from about 0.05% to about 0.50% of witch hazel extract;
        (xiv) from about 0.05% to about 0.5% of chamomile extract;
        (xv) from about 0.05% to about 0.5% of arnica extract;
        (xvi) from about 0.1% to about 0.5% of methylparaben;
        (xvii) from about 0.1% to about 0.5% of propylparaben
        (xviii) from about 0.50% to about 2% of allantoin; and
        (xix) from about 0.05% to about 0.50% of fragrance;
    wherein the pH of the emulsion is from about 3.0 to about 6.0, the allantoin being stable in the emulsion for at least 90 days at 40° C.; and
    (b) a flexible element that adsorbs or absorbs the emulsion such that the emulsion is applied to the skin of a patient on whom the flexible applicator is placed.

3. The flexible applicator system of claim 2 wherein the pH of the emulsion is from about 4.5 to about 5.8.

4. A flexible applicator system for applying an oil-in-water emulsion comprising:
    (a) an oil-in-water emulsion comprising:
        (i) from about 55% to about 75% water;
        (ii) from about 1.0% to about 2.5% of 30% sodium lauryl sulfate;
        (iii) from about 3.0% to about 6.0% of propylene glycol;
        (iv) from about 0.1% to about 0.3% of tetrasodium EDTA;
        (v) from about 0.08% to about 0.35% citric acid;
        (vi) from about 8% to about 12% lanolin oil;
        (vii) from about 3.5% to about 7.5% of cetyl alcohol;
        (viii) from about 1.0% to about 3.0% of stearyl alcohol;
        (ix) from about 1.0% to about 2.5% of beeswax,
        (x) from about 1.0% to about 4.0% of cod liver oil;
        (xi) from about 0.2% to about 0.8% of butylated hydroxytoluene;
        (xii) from about 0.05% to about 0.15% of St. John's wort extract;
        (xiii) from about 0.05% to about 0.15% of witch hazel extract;
        (xiv) from about 0.05% to about 0.15% of chamomile extract;

(xv) from about 0.05% to about 0.15% of arnica extract;
(xvi) from about 0.15% to about 0.40% of methylparaben;
(xvii) from about 0.10% to about 0.30% of propylparaben
(xviii) from about 0.50% to about 2.0% of allantoin; and
(xix) from about 0.1% to about 0.3% of fragrance;

wherein the pH of the emulsion is from about 3.0 to about 6.0, the allantoin being stable in the emulsion for at least 90 days at 40°C.; and (b) a flexible element that adsorbs or absorbs the emulsion such that the emulsion is applied to the skin of a patient on whom the flexible applicator is placed.

5. The flexible applicator system of claim 4 wherein the pH of the emulsion is from about 4.5 to about 5.8.

6. A flexible applicator system for applying an oil-in-water emulsion comprising:
(a) an oil-in-water emulsion comprising:
   (i) about 68.68% water;
   (ii) about 1.9% of 30% sodium lauryl sulfate;
   (iii) about 5.3% of propylene glycol;
   (iv) about 0.15% of tetrasodium EDTA;
   (v) about 0.12% citric acid;
   (vi) about 10.6% lanolin oil;
   (vii) about 4.2% of cetyl alcohol;
   (viii) about 2.0% of stearyl alcohol;
   (ix) about 1.90% of beeswax,
   (x) about 2.0% of cod liver oil;
   (xi) about 0.5% of butylated hydroxytoluene;
   (xii) about 0.1% of St. John's wort extract;
   (xiii) about 0.1% of witch hazel extract;
   (xiv) about 0.1% of chamomile extract;
   (xv) about 0.1% of arnica extract;
   (xvi) about 0.3% of methylparaben;
   (xvii) about 0.25% of propylparaben
   (xviii) about 1.50% of allantoin; and
   (xix) about 0.20% of fragrance;

wherein the pH of the emulsion is from about 3.0 to about 6.0, the allantoin being stable in the emulsion for at least 90 days at 40°C.; and (b) a flexible element that adsorbs or absorbs the emulsion such that the emulsion is applied to the skin of a patient on whom the flexible applicator is placed.

7. The flexible applicator system of claim 6 wherein the pH of the emulsion is from about 4.5 to about 5.8.

8. The flexible applicator system of claim 1 wherein the flexible element is in the form of a bandage.

9. The flexible applicator system of claim 2 wherein the flexible element is in the form of a bandage.

10. The flexible applicator system of claim 4 wherein the flexible element is in the form of a bandage.

11. The flexible applicator system of claim 6 wherein the flexible element is in the form of a bandage.

12. The flexible applicator system of claim 1 wherein the flexible element is in the form of a wipe.

13. The flexible applicator system of claim 2 wherein the flexible element is in the form of a wipe.

14. The flexible applicator system of claim 4 wherein the flexible element is in the form of a wipe.

15. The flexible applicator system of claim 6 wherein the flexible element is in the form of a wipe.

16. The flexible applicator system of claim 1 wherein the flexible element is formed of a material selected from the group consisting of cotton, gauze, cellulose, nylon, rayon, a non-woven fabric, and a plastic polymer.

17. The flexible applicator system of claim 2 wherein the flexible element is formed of a material selected from the group consisting of cotton, gauze, cellulose, nylon, rayon, a non-woven fabric, and a plastic polymer.

18. The flexible applicator system of claim 4 wherein the flexible element is formed of a material selected from the group consisting of cotton, gauze, cellulose, nylon, rayon, a non-woven fabric, and a plastic polymer.

19. The flexible applicator system of claim 6 wherein the flexible element is formed of a material selected from the group consisting of cotton, gauze, cellulose, nylon, rayon, a non-woven fabric, and a plastic polymer.

* * * * *